United States Patent [19]
Korenstein et al.

[11] Patent Number: 6,149,891
[45] Date of Patent: *Nov. 21, 2000

[54] X-RAY CONTRAST MEDIUM AND METHOD FOR PROTECTING AGAINST HARMFUL EFFECTS THEREOF

[75] Inventors: Rafi Korenstein, 59 Sireni Street, Rehovot, Israel, 76240; Avi Dascalu, 20 Mosenzon Street, Tel-Aviv, Israel, 62965

[73] Assignees: Israel Humanitarian Foundation Ltd., Ramat Gan; Avikam Harell, Ramat Aviv; Avi Dascalu, Tel Aviv, all of Israel; Jade Holding Inc. B.V.I, Tortola, Virgin Islands (Br.); Rafi Korenstein, Ramat Aviv, Israel

[ * ] Notice: This patent issued on a continued prosecution application filed under 37 CFR 1.53(d), and is subject to the twenty year patent term provisions of 35 U.S.C. 154(a)(2).

[21] Appl. No.: 08/952,954

[22] PCT Filed: May 24, 1996

[86] PCT No.: PCT/US96/07666

§ 371 Date: Nov. 25, 1997

§ 102(e) Date: Nov. 25, 1997

[87] PCT Pub. No.: WO96/38183

PCT Pub. Date: Dec. 5, 1996

[30] Foreign Application Priority Data

May 31, 1995 [IL] Israel ......................................... 113926

[51] Int. Cl.[7] .................................................... A61K 49/04

[52] U.S. Cl. .............................................................. 424/9.4
[58] Field of Search ............................... 424/9.1, 9.2, 9.3, 424/1.11, 1.65, 1.69, 1.73, 1.29, 9.4, 9.43, 9.5, 9.6, 9.451, 9.45, 9.41, 9.42, 9.44; 534/10, 14, 15, 16

[56] References Cited

U.S. PATENT DOCUMENTS

| | | |
|---|---|---|
| Re. 34,077 | 9/1992 | Segall et al. ............................... 604/52 |
| 4,239,747 | 12/1980 | Pfeiffer et al. ....................... 424/9.451 |
| 4,830,858 | 5/1989 | Payne et al. ............................. 424/450 |
| 5,199,951 | 4/1993 | Spears ........................................ 604/96 |
| 5,250,672 | 10/1993 | Sadler et al. ............................ 536/7.3 |
| 5,334,370 | 8/1994 | Josef et al. ................................. 424/5 |
| 5,336,762 | 8/1994 | Ranney ..................................... 534/16 |
| 5,545,397 | 8/1996 | Spielvogel et al. ...................... 424/9.4 |
| 5,591,710 | 1/1997 | Hsia ............................................ 514/6 |
| 5,851,510 | 12/1998 | Counsell et al. ....................... 424/9.45 |

OTHER PUBLICATIONS

M. Verstraete, *Primary and secondary prevention of arterial thromboembolism*, British Medical Bulletin, vol. 50, No. 4, issued Oct. 1994, pp. 946–965.

*Primary Examiner*—Jose' G. Dees
*Assistant Examiner*—Michael G. Hartley
*Attorney, Agent, or Firm*—Norris, McLaughlin & Marcus, P.A.

[57] ABSTRACT

Contrast medium injectable into the blood circulation comprising an effective amount of a contrast agent useful in X-ray imaging and a protecting agent, wherein the protecting agent is active in protecting against possible damaging effects of the contrast medium.

3 Claims, 1 Drawing Sheet

X-RAY CONTRAST MEDIUM AND METHOD FOR PROTECTING AGAINST HARMFUL EFFECTS THEREOF

This application is a 371 of PCT/US96/07666, filed May 24, 1996.

FIELD OF THE INVENTION

The present invention is generally in the field of contrast media. More specifically, the present invention relates to a contrast medium with improved patient's tolerance.

PRIOR ART

The following is a list of references which are believed to be pertinent as prior art to the present invention:
1. Hirshfeld, J. W., N. Engl. J. Med., 326, 482–484, (1989).
2. Sovak M., Handbook of Experimental Pharmacology, 73, 1–19, Springer-Verlag, Berlin (1984).
3. Gmelin E., et al., Recent developments in nonionic contrast media, pp. 67–69, Thieme Med. Pub. Inc., N.Y. (1989).
4. Scherberich, J. E., et al., Recent developments in nonionic contrast media, pp. 1–94, Thieme Med. Pub. Inc., N.Y. (1989).
5. Hou S. H., et al., Am. J. Med., 74, 243–248, (1983).
6. Schwab, S. J., et al., N. Engl. J. Med., 320, 149–153, (1989).
7. Morgan D. M. L. and Bettmann, Cardiovasc. Intervent. Radiol., 12, 154–160, (1989).
8. Hoffman E. K. and Simonsen L. O., Physiol. Rev., 69, 315–382, (1989).
9. Cala, M. C., et al., Comp. Biochem. Physiol., 90A, 551–555, (1988).
10. Busa W. B., Annu. Rev. Cell Physiol., 48, 389–402, (1986).
11. Dascalu A., Peer A., Academic Rad., 1, 145–150, (1994).

The above references will be referred to herein by indicating, within brackets, the number from the above list.

BACKGROUND OF THE INVENTION

Contrast Media (hereinafter "CM") are routinely used in various imaging procedures. Such procedures include visualization of blood vessels in cardiac angiography, either by x-ray imaging or by Magnetic Resonance Imaging (MRI), intravenous urography (kidney imaging), computerized tomography and neurologic visualization of the spinal cord, the brain, etc. In the U.S.A. alone, there are more than 10 million x-ray radiologic examinations using CM, performed each year. 5 to 10% of these procedures are accompanied by clinical side effects; in 1 out of 1000–2000 of such procedures, there occurs a life threatening complication.

The currently used CM in the x-ray imaging procedure can be grouped, on the basis of their osmolarity, to such which have a low osmolarity (hereinafter "LOCN") and such having a high osmolarity (hereinafter "HOCM"). It should be noted that both LOCM and HOCM have an osmolarity which is above that of the blood. HOCM have a typical osmolarity of about 1500–2000 mOsm/kg and LOCM have an osmolarity within the range of 300–700 mOsm/kg. Adverse side effects associated with CMs include such which result from the high osmolarity. The introduction of LOCMs, which are the new generation of CMs, was meant to counter some of these side effects. It should be noted that one big disadvantage of LOCMs is their high price-tag (about 5–10 times that of HOCM). Therefore, there is a dispute of the kinds of x-ray CMs which should be used[1].

The visualization which is the outcome of CM injection into the blood, results from a local dispersion of the high iodine atom concentration contained in the CM, from the high osmolarity, as well as from an increased viscosity in the blood vessels of the visualized organ[2]. In procedures wherein the CMs are introduced into the blood, this is achieved either by injection into the blood vessels or by catheterization.

The MRI method for visualization of blood vessels comprises the injection of a paramagnetic substance dissolved in a hyperosmotic CM to the region to be visualized.

Individuals subjected to procedures involving the use of CMs, are exposed to several hazards, depending on the CM used, including:
1. Hyperosmotic Damage:

Typically 100–200 ml of CM are injected into a total plasma volume of 5 liters within a period of several minutes. Cells such as endothelial cells, red and white blood cells, cells within the kidney, etc., are exposed to a hyperosmotic solution, reaching 200–2000 mOsm/kg at the site of injection, as compared to the osmolarity of the blood with its 300 mOsm/kg, giving rise to a hyperosmotic shock which may elicit related damages. In the following description the term "hyperosmotic CM" will refer to any CM having osmolarity higher than the blood osmolarity which is typically 300 mOsm/kg.
2. Iodine Specific Toxicity:

In an x-ray visualization procedure typically 30–40 grams of iodine (included within the contrast media) are injected into the blood within the period of 2–10 minutes. It should be noted that target visualization requires a minimum accumulation of 15–20 mg of iodine/ml in the target tissue[3] and this is the reason that the initial iodine concentration in the CM is relatively high in the range of 300–420 mg iodine/ml.
3. Kidney Damage:

The iodine load to which the kidney is exposed and which it has to secrete is a potential cause for renal damage[4]. It is generally believed today that 12% of all patients which are injected with an x-ray CM, encounter renal complications[5]. A recent study shows that during cardiac catheterization procedure, 9% of low risk and 16% of high risk patients develop renal failure[6]. Various studies made with CMs have shown that exposure of cells to x-ray CM causes the cell damages[7,8,9.10].

SUMMARY OF THE INVENTION

It is an object of the present invention to provide a novel contrast medium composition. It is particularly an object of the invention to provide a contrast medium composition with lower hazardous side effects as compared to hitherto used CM compositions.

It is more particularly the object of the present invention to provide such a composition comprising, in addition to the contrast medium, also other agents which protect tissue against damages which can be inflicted by the CM by either direct cytotoxic effects or hyperosmotic effects. According to a particular embodiment, it is the object of the present invention to provide such a composition containing endothelial and kidney cells protecting agents.

It is further the object of the present invention to provide a method for protecting tissue and organs within the body from harmful effect which may otherwise be inflicted by the CM.

In the following description, the term "contrast agent" or "CA" will be used to denote an agent which absorbs or reacts in another way with the electromagnetic irradiation used in a body visualization procedure. The CA, which is injected into the circulation, may be an agent, such as an iodine containing substance, which blocks x-ray irradiation and can thus be used for the visualization of blood vessels or other body fluid-containing organs or tissue in x-ray visualization procedure. The CA may also be a paramagnetic substance used in an MRI visualization procedure.

The term "contrast medium" or "CM" will be used to denote a liquid composition comprising a CA which is injected into the circularization prior to visualization process. The CM is typically a hyperosmotic composition.

The term "protecting agent" or "PA" will be used to denote an agent which in accordance with the present invention is incorporated into a CM, for the purpose of protecting tissue or organs, fully or partially, against some or all of the hazardous effects of CM's noted above. The CM in accordance with the present invention thus comprises both a CA and a PA.

In the following the term "effective amount" will be used to denote an amount of an agent sufficient to achieve the desired effect. In the case of a CA, the effective amount is an amount sufficient to achieve the desired contrast. In the case of a PA, an effective amount is an amount sufficient to achieve a protecting effect.

The present invention provides by a first of its aspects, a contrast medium, comprising an effective amount of a contrast agent, and an effective amount of a protecting agent being an agent active in protecting against possible damaging effects of the contrast medium, said protecting agent being one or more members selected from the group consisting of (i) non-steroidal anti-inflammatory drugs (NSAID), (ii) agents which induce cells to generate nitric oxides (NO), (iii) polysaccharides capable of sealing the intercellular spaces which exist between endothelial cells, (iv) direct anticoagulants of the heparin class and (v) anti-oxidants which are free radical scavengers.

The present invention further provides, by a second of its aspects, use of said protecting agents in the preparation of a contrast medium.

The invention still further provides, by a third of its aspects, a method for protecting an individual against harmful effects of a CM, comprising administering to the individual, together with the contrast medium, also a protecting agent as defined above.

The non-steroidal anti-inflammatory drugs (NSAID) are compounds which have an anti-inflammatory, and in addition anti-pyretic and analgesic activities. Examples of NSAID are:

Aniline derivatives such as paracetamol, phenacetin;
Anthranilic derivatives such as flufanamic acid, mefenamic acid;
Phenyl alkanoic derivatives such as fenoprofen, flurbiprofen, ibufrofen, ketoprofen;
Pyrazole derivatives such as amidopyrine, dipyrone, phenazone, phenylbutazone;
Salicylic acid derivatives such as aspirin, salicylic acid, choline salicylate.

Examples of agents which induce cells to generate nitric oxide (NO) are nitroglycerine, nitroprusside, isosorbide dinitrate and others. Polysaccharides which act in sealing the intercellular spaces between endothelial cells are agents capable of forming a coating over the walls of blood vessels and of forming a barrier between the interior of the blood vessel and the cells. An example of such an agent is dextran.

Examples of direct anti-coagulants of the heparin class are: heparin, low molecular weight heparins (such as inoxaprine) and the like.

Anti-oxidants which are free radical scavengers are useful particularly where the CA is of a kind that is capable of inducing the formation of free radicals which cause cellular damage. Examples for such agents are glutathione, tocopherols and the like.

The invention will now be illustrated in the following examples with occasional reference to the annexed drawings:

EXAMPLES

Cell Culture Preparation

Figure 1:
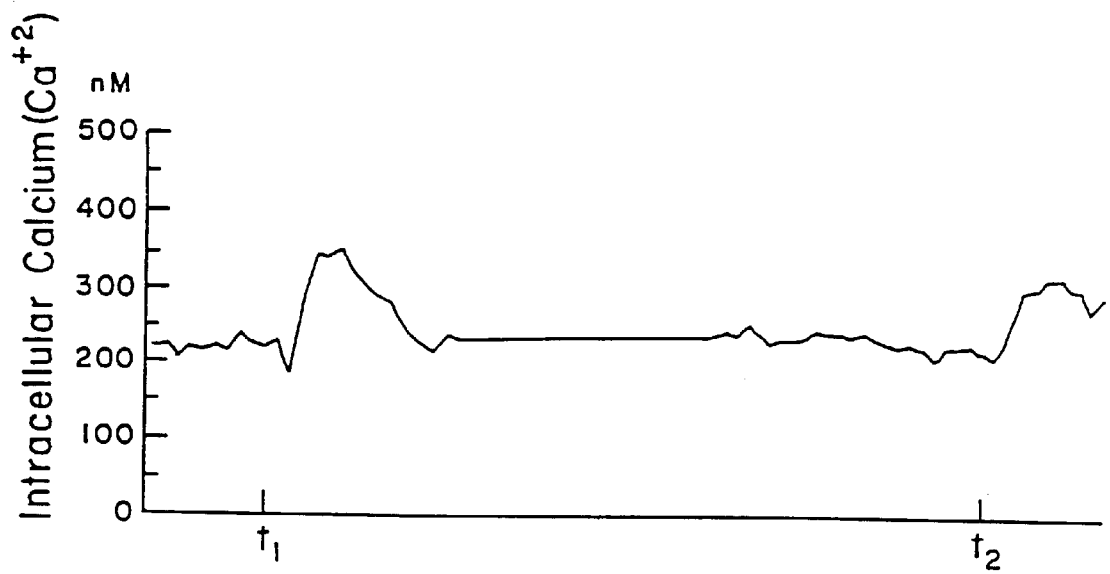
FIG. 1 shows the effect of CA (added at $t_1$ and $t_2$) on intracellular calcium endothelial cells in vitro.

Human umbilical vascular endothelial cells (HUVEC) CRL-1730 (American Type Culture Collect) were cultured according to known techniques. Briefly, HUVEC were grown in F 12K medium (Irving Scl. USA) containing 30 µg/ml Endothelial Cell Growth Factor, 100 µg/ml heparin, 10% fetal calf serum and 5% neonatal calf serum. Cells were seeded at an initial density of $1-2\times10^5$ cells/cm$^2$ and kept at 37° C. under an atmosphere of 5% $CO_2$ in air. To all such mediums, 4.5 mg/ml glutamine, 50 units/ml penicillin, 200 µgml of streptomycin and 1250 units/mi nystatin were added. Media were changed twice weekly and cells were grown for about 7–10 days until confluence. Confluent cells were trypsinized and experiments were performed when trypan blue was excluded from 95% or more of the cells.

Measuring Techniques
Image Analysis Procedures and Calibration

[$Ca^{+2}$] analysis was performed by using an Applied Imaging Magical system (TARDIS version 7.3). Cover slips with attached endothelial cells in the epifluorescence mode (oil-immersion objective, X 40) and equipped with a xenon lamp. Intracellular calcium measurements were assayed by ratio imaging of FURA-2/AM (excitation, 340 and 380 nm; emission, 515 nm). A temperature-controlled cell perfusion chamber (Applied imaging) was used to keep cells at a temperature of 32° C. All solutions were maintained at 32° C. in a temperature controlled bath. Single cell images (10–40 cells) were collected by an intensified video camera (Photonic Science). The video signal was averaged over 4 video frames and averaged image pairs (340 and 380 nm) were captured every 5–15 seconds. Images were digitized at 256×256 pixels and averaged after subtracting the background.

Intracellular calcium calibration: Fura-2/AM signals were calibrated by addition of lonomycin (5 µM) to cells kept in a 2 mM $Ca^{+2}$ solution to obtain maximum fluorescence. An addition of 10 mM of [ethylene-bis-(oxyethylenenitrilo)]-tetraacetic acid) (EGTA) followed in order to adjust the pH to >8.5 in order to obtain the minimal fluorescence. The intracellular calcium was calculated as previously described employing a $Ca^{+2}$-Fura 2 dissociation constant of 224 nM.

Tetrazolium Salt Assay

The 3-[4,5-Dimethythiazol-2-yl]-2,5-diphenyltetrazolium bromide (MTT) colorimetric reaction is based on the uptake of tetrazolium salt exclusively by live cells and its reduction to a soluble violet (formazan) compound. Absorbance of formazan is proportional to the amount of active mitochondrial enzyme succinate-dehydrogenase of the cells and consequently to cell viability. Both endothelial or kidney cells were seeded at 30000–40000 cells/well in 96-well microliter wells (Corning) and grown until confluence. The measurements were performed after statistically testing the assumption that endothelial cells as well as the kidney cell line display contact inhibited cell growth, therefore yielding about equal cell numbers in each well. The absorbance spectrum of MTT was determined by a diode array spectrophotometer (Hewlett Packard, 8452A). MTT exhibited peak absorbance at 560 nm and minimal readings beyond 620 mn, as previously shown. A microplate reader (Thermomax, Molecular Devices) was used to read absorbance at 550 nm with background subtraction at a reference absorbance of 650 nm at 25° C.

The experiments employed confluent cells which were loaded with 0.15 µg/ml of MTT and dark incubated at 37° C. Four hours later the medium was removed by plate flipping and 100 µg/ml DMSO were added to each well in order to solubilize the formazan crystals. Results are expressed in percentages as compared to control values of untreated cells and each result consisted of four to six repeated measurements in at least two different experiments. HUVEC cells were exposed to CM for either 4 or 24 hours prior to optical density readings.

PRIOR ART REFERENCE EXPERIMENTS

The cytotoxic effect of CA materials on these cells was hitherto evaluated by Dascalu and Peer (1994)[11], in a series of experiments wherein the viability of the cells was determined in the presence or absence of CA. This evaluation was done by determining the tetrazolium salt (MTT) which was reduced to violet formazan as will be further elaborated. This reaction required the activity of mitochondrial dehydrogenase and thus is indicative of cell viability. The results presented there show that both endothelial and kidney cells are damaged when exposed to CA for 4 hours.

Example 1

The effect of using PA in conjunction with CA materials was evaluated by determining the cytotoxic effect and intracellular calcium levels in endothelial cells with or without PA.

The effect of CA (in this case Telebrix™, (Guerbet, France)) can be seen in FIG. 1. As can be seen, upon addition of 35 µl of CA into 1 ml of hepes-buffered saline at $t_1$, there is an immediate increase in the intracellular calcium level. The calcium level increase also occurs upon re-addition of the same CA at $t_2$.

Figure 2:
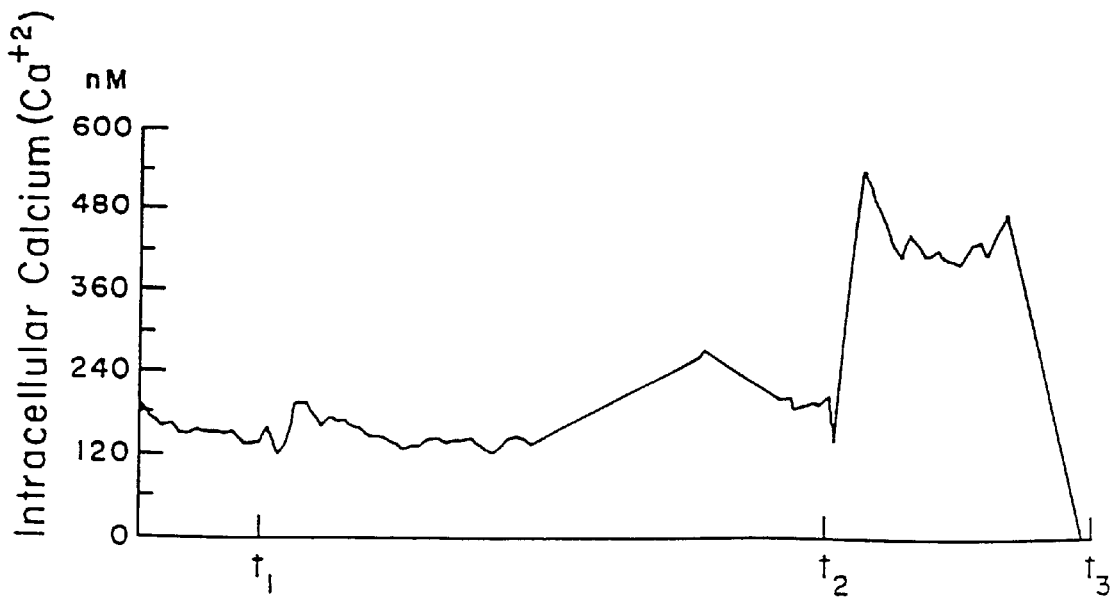
FIG. 2 demonstrates the effect of the combination of PA and CA upon the intracellular calcium (CA and PA were added together at $t_1$ then washed and then CA was added separately at $t_2$).

When a CA as described above was administered together with indomethacin, as shown in FIG. 2 (at $t_1$), there was no or negligible increase in the intracellular calcium level. Upon re-administration of the CA, at $t_2$, after the CA and indomethacin were washed out, there was a marked increase in the intracellular calcium level. This demonstrates the protective effect which indomethacin has on such harmful effects of the CA.

Example 2

Endothelial cell viability was tested upon 4 hours of exposure to CA with or without a protecting agent (PA). The results are shown in the following Table 1:

TABLE 1

| CA*  | PA** | CA only   | CA + PA    |
|------|------|-----------|------------|
| CA1  | A    | 142 ± 17  | 199 ± 40   |
| CA1  | A    | 228 ± 26  | 265 ± 29   |
| CA1  | A    | 407 ± 52  | 452 ± 43   |
| CA1  | A    | 707 ± 53  | 768 ± 16   |
| CA2  | A    | 678 ± 94  | 835 ± 62   |
| CA2  | A    | 315 ± 38  | 369 ± 38   |
| CA3  | A    | 774 ± 103 | 929 ± 64   |
| CA3  | A    | 602 ± 73  | 752 ± 134  |
| CA3  | B    | 884 ± 99  | 1059 ± 205 |
| CA2  | B    | 355 ± 18  | 402 ± 56   |
| CA4  | B    | 124 ± 24  | 228 ± 62   |
| CA2  | C    | 678 ± 94  | 800 ± 85   |
| CA4  | C    | 244 ± 23  | 292 ± 31   |
| CA1  | D    | 856 ± 69  | 934 ± 55   |
| CA2  | D    | 678 ± 94  | 825 ± 65   |
| CA1  | E    | 707 ± 53  | 812 ± 44   |
| CA1  | E    | 583 ± 55  | 769 ± 32   |
| CA1  | E    | 228 ± 26  | 297 ± 41   |
| CA3  | E    | 602 ± 73  | 802 ± 141  |

*CA1 = Ultravist, Schering, AG, Germany
CA2 = Hexabrix-320, Guerbet, France
CA3 = Omnipaque, Schering AG, Germany
CA4 = Conray-60, Malinckrodt, U.S.A.
**A = Indomethacin (50 micromolar)
B = Heparin (100 units/ml)
C = Dextran (50 microgram/ml)
D = Nitroprusside (50 micromolar)
E = Glutathione (2 mM).

The average and the standard deviations of the absolute optical density readings of formazan absorption of light are presented in the above Table. The results given, reflect the mitochondrial activity of the tested cells, and serve as an indicative tool to evaluate the cells viability.

What is claimed is:

1. A blood circulation injectable contrast medium, comprising an effective amount of a contrast agent used for X-ray imaging, and an effective amount of a protecting agent being an agent active in protecting against possible damaging effects of the contrast medium, said protecting agent being one or more members selected from the group consisting of:

(ii) agents which induce cells to generate nitric oxides (NO).

2. A method for protecting an individual against harmful effects of contrast media in an X-ray imaging procedure involving injection into the blood circulation of said individual of a contrast medium, comprising injecting into the individual a contrast agent used for X-ray imaging in combination with a protecting agent being a member of the group consisting of:

(ii) agents which induce cells to generate nitric oxides (NO).

3. A method for preparing a blood circulation injectable contrast medium comprising adding to an effective amount of a contrast agent used for X-ray imaging and an effective amount of a protecting agent being an agent active in protecting against possible damaging effects of the contrast medium, said protecting agent being one or more members selected from the group consisting of:

(ii) agents which induce cells to generate nitric oxides (NO).

* * * * *